(12) United States Patent
Wang et al.

(10) Patent No.: US 8,968,541 B2
(45) Date of Patent: Mar. 3, 2015

(54) RAPID ELECTROPHORESIS BINDING METHOD AND RELATED KITS AND COMPOSITIONS

(75) Inventors: Zhuying Wang, Monmouth Junction, NJ (US); Jinyu Yang, Nanjing (CN); Fanli Meng, New York, NY (US); Bing Lai, Nanjing (CN); Zhan Dai, Nanjing (CN); Fang Liang Zhang, Fanwood, NJ (US)

(73) Assignee: Nanjingjinsirui Science & Technology Biology Corp., Nanjing (CN)

( * ) Notice: Subject to any disclaimer, the term of this patent is extended or adjusted under 35 U.S.C. 154(b) by 738 days.

(21) Appl. No.: 12/797,011

(22) Filed: Jun. 9, 2010

(65) Prior Publication Data

US 2010/0326828 A1    Dec. 30, 2010

Related U.S. Application Data

(60) Provisional application No. 61/302,213, filed on Feb. 8, 2010, provisional application No. 61/221,230, filed on Jun. 29, 2009.

(51) Int. Cl.
  *B01D 57/02*   (2006.01)
  *G01N 33/559*   (2006.01)
  *G01N 27/447*   (2006.01)

(52) U.S. Cl.
  CPC .............. *G01N 27/44726* (2013.01)
  USPC .......................................... 204/466; 204/463

(58) Field of Classification Search
  USPC ................. 204/463, 464, 466, 467, 613, 614; 436/164, 516
  See application file for complete search history.

(56) References Cited

U.S. PATENT DOCUMENTS

| | | | | |
|---|---|---|---|---|
| 3,966,897 | A * | 6/1976 | Renn et al. | 436/515 |
| 4,021,324 | A * | 5/1977 | Delony et al. | 204/463 |
| 4,693,804 | A * | 9/1987 | Serwer | 204/466 |
| 6,277,259 | B1 * | 8/2001 | Guttman et al. | 204/461 |
| 2006/0275917 | A1 * | 12/2006 | Wada | 436/174 |

FOREIGN PATENT DOCUMENTS

WO   WO 2004011926 A1 *   2/2004

OTHER PUBLICATIONS

Fazekas et al, "Two new staining procedures for quantitative estimation of proteins on electrophoretic strips", Biochim. Biophys. Acta., vol. 71, pp. 377-391 (1963) (Abstract Only).

* cited by examiner

*Primary Examiner* — Luan Van
*Assistant Examiner* — Maris R Kessel
(74) *Attorney, Agent, or Firm* — Panitch Schwarze Belisario & Nadel LLP

(57) ABSTRACT

An improved staining method is described for staining a biopolymer such as a peptide, a protein, an RNA, a DNA, an oligosaccharide or a complex containing a peptide, a protein, an RNA, a DNA, or an oligosaccharide in a matrix. The method includes the step of moving a staining reagent into the matrix using an electric force. The staining time can be dramatically reduced relative to conventional technologies. The improved staining method can particularly be used, for example, to stain proteins after gel separation. Other related methods and related kits are also described.

19 Claims, 4 Drawing Sheets

Quick staining for 6 minutes

Fix for 1 hr    Stain for 1 hr   Destain for 3 hrs

Quick staining for 6 minutes

RAPID ELECTROPHORESIS BINDING METHOD AND RELATED KITS AND COMPOSITIONS

CROSS-REFERENCE TO RELATED APPLICATION

This application is entitled to and claims the benefit of the priority pursuant to 35 U.S.C. §119(e) of U.S. Provisional Patent Application No. 61/221,230, filed Jun. 29, 2009, and U.S. Provisional Patent Application No. 61/302,213, filed Feb. 8, 2010, the disclosure of which is hereby incorporated by reference in its entirety.

FIELD OF THE INVENTION

The invention relates to a method for rapidly binding a binding agent to a biopolymer such as a peptide, a protein, an RNA, a DNA, an oligosaccharide or a complex thereof in a matrix by moving the binding agent into the matrix using an electric force, thereby binding the binding agent to the biopolymer in the matrix. In a particular embodiment, the invention relates to methods and kits and compositions useful for performing rapid staining of proteins or peptides resolved by polyacrylamide gel electrophoresis (PAGE).

BACKGROUND OF THE INVENTION

Biopolymers such as peptides, proteins, nucleic acids (RNA or DNA), oligosaccharides, or complexes thereof are commonly analyzed by gel electrophoresis. Usually samples of interest are loaded in a matrix such as a polyacrylamide gel and exposed to an electric field which causes various components in the sample to migrate and separate into distinct bands according to the molecular weight, net charge, size, and other physical and chemical properties of the molecules and the pore size of the matrix. After electrophoresis, different biopolymers embedded at different locations on the matrix can be further characterized by their interactions with or bindings to one or more binding agents, such as staining reagents.

Numerous methods and reagents have been developed to visualize or detect the biopolymers of interest within a matrix such as a gel. These include staining reagents that can be classified into five classes. The first class of staining reagents includes organic dyes that bind to biopolymers, such as Coomassie Blue dyes that stain proteins and make the protein bands blue, which can be subsequently visualized by naked eyes. The second class of staining reagents includes fluorescent dyes that bind to biopolymers, such as ethidium bromide that stains DNA or RNA and makes the stained DNA or RNA bands red when shined with UV light. The third class of staining reagents includes silver staining reagents. The fourth class of staining reagents includes staining reagents that stain the background, which are also called negative staining reagents. The fifth class of staining reagents includes biological molecules and their derivatives, such as antibodies and antibody-based reagents that bind to antigens, which are also called immunostaining reagents, or labeled polynucleotide that binds to complementary DNA or RNA. The second and third classes of staining reagents were developed to increase the sensitivity over that achieved with the organic dyes of the first class.

Coomassie Blue staining was introduced in early 1960s by Fazekas, et al. as a method for visualizing proteins in the gels (*Biochim. Biophys. Acta* 71:377, 1963). In addition to Coomassie Blue, other organic dyes such as Amido black, Ponceaus S, Fast green FCF, zincon, Eriochrome black T, etc., have also been used to stain proteins. However, Coomassie Blue staining is still widely used and remains the most commonly used general method for protein staining and detection.

Typically, a conventional method for Coomassie Blue staining of proteins embedded in a gel comprises the following steps: (i) fixing the gel in Fixing Solution for 1 hour (hr) with gentle agitation; (ii) staining the gel from Step (i) in Staining Solution for 1 hr with gentle agitation; and (iii) destaining the gel from Step (ii) in Destaining Solution. The Destaining Solution is replaced several times during the destaining step until the background of the gel is fully destained, which usually takes 2 to 3 hours or even overnight.

Staining proteins with organic dyes is relatively inexpensive, takes less time than silver staining, but it still takes a few hours or even overnight. For example, the above described conventional method of Coomassie Blue staining takes about 3 hours or more with at least 3 steps, thus is time consuming and cumbersome. Improvements have been made in Coomassie Blue protein staining methods, e.g., by using new staining reagents such as Colloidal Coomassie Blue, or by performing the incubation in a microwave to enhance staining and reduce the incubation time. However, the three basic steps of fixing, staining and destaining are still necessary to obtain satisfactory results.

Immunostaining of antigens in a matrix, such as a polyacrylamide gel, also takes many steps and multiple solutions. Each step may take minutes to hours to complete, in part because the staining reagents, e.g., antibodies and antibody-based reagents, diffuse into the matrix slowly. Similarly, the hybridization of a polynucleotide with another polynucleotide, such as the Southern or Northern blotting, is also time consuming.

Thus, there is still a need for a simple and rapid process for staining a biopolymer, such as a peptide, a protein, an RNA, a DNA, an oligosaccharide or a complex thereof. Embodiments of the present invention relate to such a process for staining, thus detection, of biopolymers embedded in a matrix with reduced time and costs.

BRIEF SUMMARY OF THE INVENTION

It is now discovered that an electric force can be used to move a binding agent, such as a staining reagent, into a matrix embedded with a biopolymer to thus bind the binding agent to the biopolymer in the matrix, stain or label the biopolymer with significantly reduced time and costs.

The binding method can be performed with a binding system interposed between a positive electrode and a negative electrode. The electric force moves a binding agent, such as a staining reagent, through the matrix, and the binding agent collides with, thus reacts with or binds to, a biopolymer embedded in the matrix, thus staining or labeling the biopolymer. The voltage applied to the electrodes can be adjusted for quick movement of the binding agent to significantly reduce the incubation time needed for its binding to the biopolymer.

According to embodiments of the present invention, the three steps of the conventional method of Coomassie Blue protein staining, i.e., the fixing, staining and destaining steps described above, are now accomplished by a single step, i.e., applying an electric force to the staining reagent. The electric force moves the staining reagent into the polyacrylamide gel to thus stain the protein in the gel, and further moves the free excess staining reagent out of the polyacrylamide gel to thus destain the gel. The time required for Coomassie Blue protein staining is now reduced to less than 10 minutes. In addition to protein staining, such method is also applicable for the interacting, reacting, binding or staining of other target molecules.

In one general aspect, the present invention relates to an integrated method for interacting a charged molecule with a target molecule. The method comprises moving the charged molecule with an electric force into a matrix embedded with the target molecule, so that the charged molecule interacts with the target molecule in the matrix.

Another general aspect of the present invention relates to an integrated method for reacting a charged molecule with a target molecule. The method comprises moving the charged molecule with an electric force into a matrix embedded with the target molecule, so that the charged molecule reacts with the target molecule in the matrix.

Another general aspect of the present invention relates to an integrated method for binding a charged molecule to a target molecule. The method comprises moving the charged molecule with an electric force into a matrix embedded with the target molecule, so that the charged molecule binds to the target molecule in the matrix.

Yet another general aspect of the invention relates to an integrated method for staining a target molecule with a charged molecule. The method comprises moving the charged molecule with an electric force into a matrix embedded with the target molecule, so that the charged molecule stains the target molecule in the matrix.

In one general aspect, the present invention relates to a method of binding a binding agent to a biopolymer embedded in a matrix. The method comprises applying an electric force to a binding agent to move the binding agent into the matrix, thereby binding the binding agent to the biopolymer embedded in the matrix, and to move excess free binding agent out of the matrix.

In one particular embodiment, the present invention relates to a method of staining a biopolymer embedded in a matrix. The method comprises applying an electric force to a staining reagent to move the staining reagent into the matrix, thereby staining the biopolymer embedded in the matrix with the staining reagent, and to move excess free staining reagent out of the matrix, thereby destaining the matrix.

In an embodiment of the presently described method of binding a binding agent to a biopolymer embedded in a matrix, the method comprises:

assembling a binding system comprising:
(i) a first solid porous material absorbed with a binding solution comprising a binding agent;
(ii) the matrix embedded with the biopolymer; and
(iii) optionally one or more solid porous materials absorbed with one or more buffer solutions,
interposing the binding system between a pair of electrodes; and
connecting the pair of electrodes to a power supply for establishing an electric force sufficient to move the binding agent into the matrix, thereby binding the binding agent to the biopolymer in the matrix, and to move excess free binding agent out of the matrix.

In an embodiment of the presently described method of staining a biopolymer embedded in a matrix, the method comprises:

assembling a staining system comprising:
(i) a first solid porous material absorbed with a staining solution comprising a staining reagent;
(ii) the matrix embedded with the biopolymer; and
(iii) optionally one or more solid porous materials absorbed with one or more buffer solutions,
interposing the staining system between a pair of electrodes; and
connecting the pair of electrodes to a power supply for establishing an electric force sufficient to move the staining reagent into the matrix, thereby staining the biopolymer in the matrix, and to move excess free staining reagent out of the matrix, thereby destaining the matrix.

Yet another general aspect of the present invention relates to a kit for binding a binding agent to a biopolymer. In a particular embodiment, the present invention relates to a kit for staining a biopolymer. The kit comprises:
a staining solution comprising a staining reagent;
optionally one or more buffer solutions; and
instructions for using the staining solution and optionally the buffer solutions for staining the biopolymer in the matrix utilizing an electric force applied to the staining reagent.

In one embodiment of the present invention, the staining solution or the optionally one or more buffer solutions are pre-absorbed in one or more solid porous materials and the pre-absorbed solid porous materials are provided in the kit.

The binding agent or staining reagent can be any type of reagent suitable for the present invention, including, but not limited to, an organic or inorganic reagent, a dye or a dye-labeled reagent, a fluorescent molecule, a radioactive or radioactive-labeled reagent, an antibody or an antibody-based reagent, a labeled polypeptide or ligand, or a labeled polynucleotide.

The matrix used in embodiments of the present invention can be composed of any type of matrix material suitable for the present invention, including, but not limited to, an agarose gel, polyacrylamide gel, or any other suitable porous materials.

The biopolymer is selected from the group consisting of a peptide, a protein, an RNA, a DNA, an oligosaccharide, and a complex thereof. It is understood by those skilled in the art that modified biopolymers or derivatives of biopolymers can also be readily labeled or strained, thus detected, by the present methods in view of the present disclosure.

According to embodiments of the present invention, the biopolymer is a protein or peptide, the matrix is a sodium dodecyl sulfate or native polyacrylamide gel, and the staining reagent is a polypeptide-staining reagent selected from the group consisting of an organic dye, an inorganic dye, a fluorescent dye, a metal-complex dye, an antibody, and a labeled polypeptide or ligand, and the polypeptide-staining reagent is absorbed in a solid porous material.

In a particular embodiment of the present invention, the biopolymer is a protein or peptide, the matrix is polyacrylamide gel, and the staining reagent is Coomassie Blue.

In another particular embodiment of the present invention, the biopolymer is a protein or peptide, the matrix is polyacrylamide gel, and the staining reagent is an antibody or an antibody-based reagent.

Embodiments of the present invention also relate to staining a biopolymer embedded in a matrix with two or more staining reagents.

The details of embodiments of the disclosure are set forth in the accompanying drawings and the description below. Other features, objects, and advantages will be apparent from the description and drawings, and from the claims.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited by the drawings.

In the drawings.

DETAILED DESCRIPTION OF THE INVENTION

Figure 1:
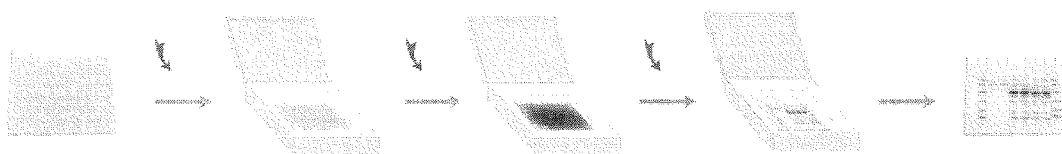
FIG. 1 schematically illustrates a conventional Coomassie Blue staining procedure.

Unless defined otherwise, all technical and scientific terms used herein have the same meaning as is commonly understood by one of skill in the art to which this invention belongs. All publications and patents referred to herein are incorporated by reference.

Embodiments of the present invention relate to methods, kits and compositions useful for rapid staining of biopolymers in matrix. In one aspect, the invention relates to a significant improvement of the conventional biopolymer staining techniques. For example, the present invention provides an improved protein staining method whereby several steps in the conventional Coomassie Blue staining procedure are reduced to one step.

According to embodiments of the present invention, an electric force moves a charged staining reagent into a matrix embedded with a biopolymer via a positive electrode and a negative electrode connected to a staining system. Depending on the voltage applied on the two electrodes, the electric force can move the staining reagent much faster than diffusion that governs the movement of the staining reagent in the conventional staining methods. The electric force can not only facilitate the quick movement of the staining reagent into the matrix to label or stain the embedded biopolymer, but also facilitate the quick movement of the excess free staining reagent out of the matrix to thereby destain the matrix. Therefore, methods according to embodiments of the present invention greatly reduce the time for staining, thus detection, of a biopolymer, at significantly reduced costs.

As used herein, the terms "binding", a "binding agent", "staining", a "staining reagent", a "biopolymer", and a "matrix" are to be taken in their broadest context.

As used herein, the term "binding" or "bind" refers to an interaction between a binding agent and a target molecule, such as a biopolymer, that results in a stable association in which the binding agent and the target molecule are in close proximity to each other. In the stable association, the binding agent and the target molecule can be interacting with each other non-covalently and covalently, the binding agent and the target molecule can be unmodified, the binding agent and the target molecule can also be modified as a result of a chemical reaction occurred during the binding process. Examples of the binding interactions include, but are not limited to, biopolymer-staining reagent interaction, protein-protein interaction, protein-peptide interaction, protein-antibody interaction, protein-small molecule interaction, protein-polynucleotide interaction, polynucleotide-polynucleotide interaction, etc.

As used herein, the term "binding agent" refers to any agent that can bind to a target molecule. The binding agent is movable by an electric force in a matrix. Examples of the binding agent to a biopolymer include, but are not limited to, a staining reagent, another biopolymer, an organic molecule, an inorganic molecule, etc.

As used herein, the term "staining" refers to a process in which a staining reagent reacts with, covalently or non-covalently binds to, or otherwise labels a biopolymer for the visualization, detection, or otherwise qualification or quantification of the biopolymer. The term "staining" encompasses "labeling", although it is not limited to "labeling."

A "staining reagent" refers to any reagent that can be used to stain or label a biopolymer by any mechanism. The staining reagent is movable by an electric force in a matrix. For example, a "staining reagent" can stain a biopolymer by a chemical reaction with the biopolymer. It can also stain the biopolymer by binding to the biopolymer, covalently or non-covalently. A "staining reagent" can be any colored or colorless substance that is detectable by a detection method. For example, a staining reagent includes, but is not limited to, an organic dye, an inorganic dye, a fluorescent dye, a metal-complex dye, a radioactive or radioactive-labeled molecule, or a colorless substance that changes color, becomes fluorescent, or otherwise becomes detectable after it binds to the biopolymers. A staining reagent can be in a pure form, or it can also exist in a mixture or solution. A staining reagent can be in a modified form (e.g., modified by a chemical) or unmodified form. The staining reagents also include a biological molecule or derivative thereof, such as an antibody or an antibody-based reagent used for immunostaining, a peptide used in ligand binding, a polynucleotide using in nucleotide hybridization, etc.

A "biopolymer" includes, but is not limited to, a peptide, a protein, an RNA, a DNA, an oligosaccharide, a complex thereof, or a modification or derivative thereof. Examples of the complex include, but are not limited to, a polypeptide-polypeptide complex, an RNA-polypeptide complex, a DNA-polypeptide complex, a polynucleotide-polynucleotide complex, etc.

In one general aspect, the present invention relates to a method of staining a biopolymer embedded in a matrix with reduced steps and time as compared to the conventional staining method. For example, as illustrated in FIG. 1, the conventional protein staining method is usually comprised of the three steps, i.e., a fixing step, a staining step and a washing step. Each of these steps is necessary in the conventional protein staining in order to obtain acceptable results. In contrast, an embodiment of the present invention provides a staining method whereby the three steps of conventional staining are combined into one step, with the use of an electric force that moves the staining reagent into the matrix, thereby staining the biopolymer, such as a protein, embedded in the matrix, and to move excess free staining reagent out of the matrix, thereby destaining the matrix. The method according to the embodiment of the present invention has greatly cut down the time required for biopolymer staining.

Embodiments of the invention relate to compositions useful in biopolymer staining. One of the compositions is a staining solution, i.e., a solution comprising one or more staining reagents.

In one embodiment of the invention, a staining solution comprises, for example, Coomassie Blue, sodium phosphate, potassium chloride, isopropanol, Tris, EDTA and acetic acid. Each of these elements can be substituted with similar elements known in the art that function in a solution in substantially the same way. Isopropanol, for example can be substituted with methanol or ethanol or other agents known in the art. Coomassie Blue can be substituted with one or more other protein staining dyes such as Amido black, Ponceaus S, Fast green FCF, zincon, Eriochrome black T, etc.

In one embodiment of the invention, the staining solution comprises about 0.1 gram to 5 grams, typically about 1 gram, Coomassie Blue (either R-250 or G-250) per liter of the staining solution.

In another embodiment of the invention, the staining solution comprises about 10 grams to 500 grams, typically about 200 grams, isopropanol per liter of the staining solution.

In yet a further embodiment of the invention, the staining solution comprises about 10 grams to about 300 grams, typically about 150 grams, acetic acid per liter of the staining solution.

In yet a further embodiment, the staining solution comprises about 0.1 gram to about 10 grams, typically about 1 gram, EDTA per liter of the staining solution.

In yet a further embodiment, the staining solution comprises about 0.1 gram to about 10 grams, typically about 1 gram, Tris per liter of the staining solution.

In yet a further embodiment, the staining solution comprises about 0.1 gram to about 10 grams, typically about 1 gram, sodium chloride per liter of the staining solution.

In yet a further embodiment, the staining solution comprises about 0.1 gram to about 10 grams, typically about 1 gram, sodium phosphate per liter of the staining solution.

In one embodiment, the pH of the staining solution is in the range of about 2.0-about 11.0, typically about 5.0.

A staining solution according to embodiments of the invention can be bottled and used as typically done in research and diagnostic laboratories. It can also be pre-absorbed to a solid porous material, such as a piece of filter paper, blotting paper, a pad, e.g., paper pad, or the like. The staining solution can be included in an article of manufacture or kit for use in biopolymer staining, such as in protein staining, and the like.

Other solutions can also be used in addition to the staining solution described above in view of the present disclosure. One or more of the ingredients in the staining solution can be omitted. On the other hands, one or more of other reagents can be added to the staining solution. The purpose of the staining solution is to improve the staining efficiency, which allows combining the fixing step, staining step and destaining step into a single step. Other solutions which serve similar functions can be developed and used in view of the present disclosure.

Other staining reagents can also be used to stain proteins in addition to the staining reagent illustrated above, such as Coomassie Blue, either R-250 or G-250. These other staining reagents include, but are not are limited to, Amido black, Ponceaus S, Fast green FCF, zincon, Eriochrome black T, calconcarboxylic acid, methyl violet, Meldola's blue, methyl orange, Fsat green, Ferrozine, Ferene S, etc.

Fluorescent staining reagents can also be used to stain proteins. These fluorescent staining reagents include, but are not are limited to, Rhodamine, Sypro series, Deep Purple, etc. It is noted that some staining reagents can become fluorescent before or after binding to proteins.

Metal ion or metal-complex (also called metal chelates) staining reagents can also be used to stain proteins. These staining reagents include, but are not are limited to, Ferrocyanide, indium- or molybdenum-pyrogallol red complex, or other metal complexes formed with pyrocatechol violet, bromopyrogallol red, xylenol orange, pyrogallol phthalein, etc. It should be noted that some of this kind of staining reagents are fluorescent or will become fluorescent after binding to proteins.

Antibodies or antibody-binding or antibody-based reagents can also be used to stain proteins by immunostaining. These staining reagents include, but are not are limited to, primary antibodies, secondary antibodies, Protein A, Protein G, Protein L, Protein A/G, tag or reporter molecule-labeled primary antibodies, secondary antibodies, Protein A, Protein G, Protein L, Protein A/G. Tag or reporter molecules include, but are not are limited to, horseradish peroxidase (HRP), alkaline phosphaste (AP), beta-galactosidase or other enzymes, radioactive isotope of iodine or other isotopes, fluorochromes which can be detected by fluorescence microscope or fluorometer, luminochromes which can be detected by luminescence methods.

A labeled peptide or ligand can also be used to label a binding partner or receptor for the peptide or ligand embedded in a matrix. Preferably, the matrix is a native polyacrylamide gel.

It is apparent to those skilled in the art that the present invention includes modifications to the above-mentioned embodiments to further improve the staining sensitivity. These modifications include, but are not are limited to, adding one or multiple steps to the above embodiment. For example, one can add a destaining step to further decrease background when higher sensitivity is desired.

A variety of methods can be used to set up the quick staining assays in view of the present disclosure. For example, a staining system can be assembled and interposed between a pair of electrodes. The staining system comprises:

(i) a solid porous material absorbed with a staining solution comprising a staining reagent;

(ii) a matrix embedded with a biopolymer; and (iii) optionally one or more solid porous materials absorbed with one or more buffer solutions.

After the staining system is interposed between a pair of electrodes, the electrodes are connected to a power supply for establishing an electric force sufficient to move the staining reagent into the matrix, thereby staining the biopolymer in the matrix, and to move excess free staining reagent out of the matrix, thereby destaining the matrix.

Figure 5:
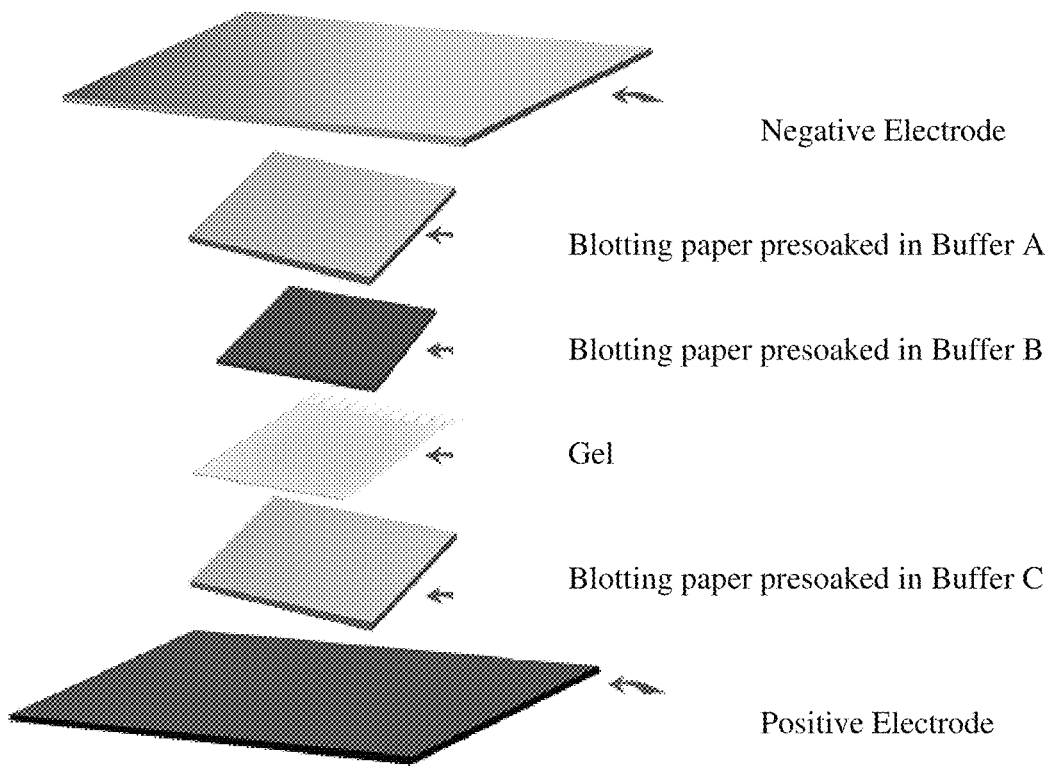
FIG. 5 schematically illustrates the sandwich setup of a quick Coomassie Blue staining procedure according to an embodiment of the invention.
Figure 6:
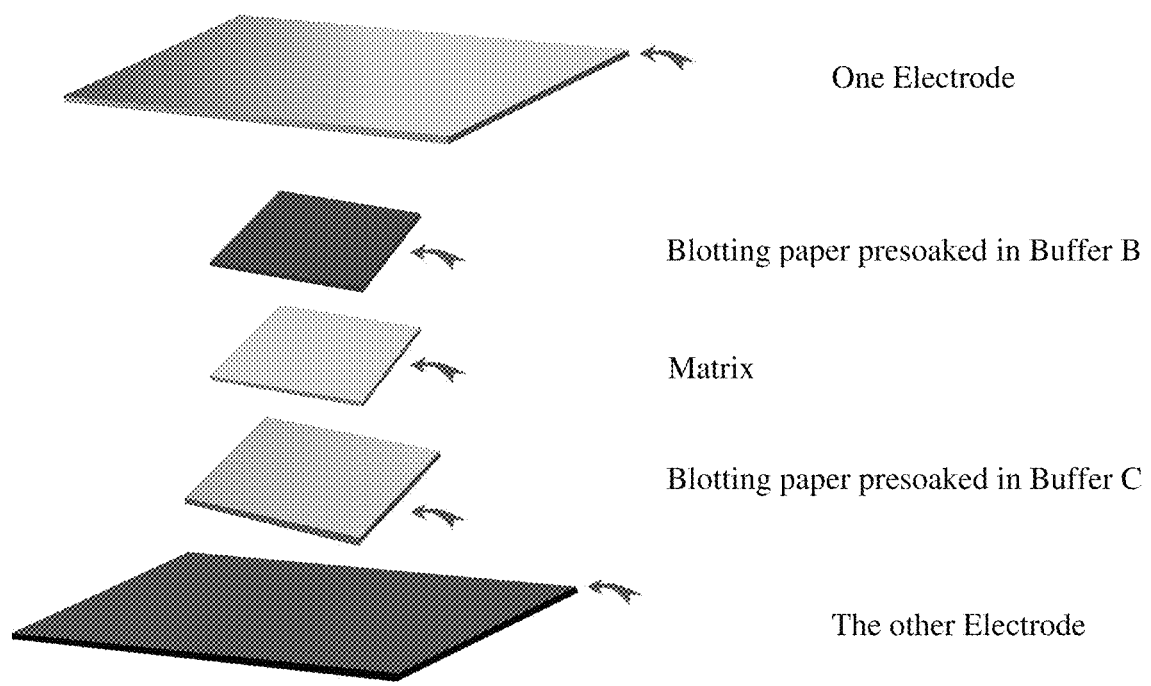
FIG. 6 schematically illustrates the sandwich setup of a quick Coomassie Blue staining procedure according to another embodiment of the invention.

According to embodiments illustrated in FIGS. 5 and 6, the staining reagent according to an embodiment of the present invention is pre-absorbed in a piece of blotting paper and placed on top of a gel embedded with proteins to be stained. If the staining reagent is positively charged, it can be pre-absorbed in a piece of blotting paper and placed just under the gel to be stained. When the electricity is turned on, the positively charged staining reagent will move up into the gel matrix and stain the proteins embedded there. It should be noted that a mixture of different staining reagents can also be used to improve staining sensitivity. It is also feasible to use the negatively charged staining reagent or mixture and the positively charged staining reagent or mixture at the same time, i.e., by separating the negatively charged staining reagent and the positively charged staining reagent with the gel matrix before staining.

In the above-mentioned embodiments, those skilled in the art will know that there are a variety of methods to position the two electrodes in view of the present disclosure. In the embodiment shown in FIG. 5, the positive electrode is at the bottom, while the negative electrode is on the top. The positions of the two electrodes can be switched. However, the position of the staining reagent should also be changed so that staining reagent will move into the gel matrix and stain the proteins. The voltage of the electricity applied to the staining apparatus can varies from 1 to 50 V.

In a preferred embodiment, the electric force moves the staining reagent in a direction that the free excess staining reagent enters the matrix and travels the least distance in the matrix before it leaves the matrix as compared to the other directions. For example, in FIG. 5, the staining reagent in Buffer B is moved into the gel in a direction transverse to the gel surface and travels a distance equal to the thickness of the gel before it leaves the gel. The thickness of the gel is the smallest compared to the other dimensions, e.g., length and width, of the gel.

However, the electric force can also move the staining reagent in other directions according to embodiments of the present invention.

Figure 2:
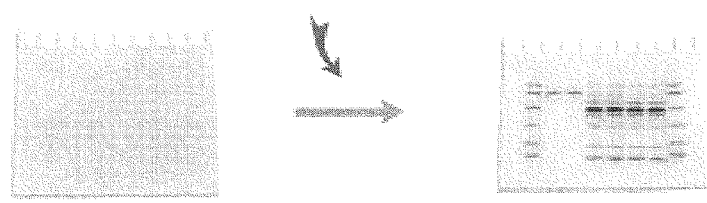
FIG. 2 schematically illustrates a quick Coomassie Blue staining procedure according to an embodiment of the invention.
Figure 3:
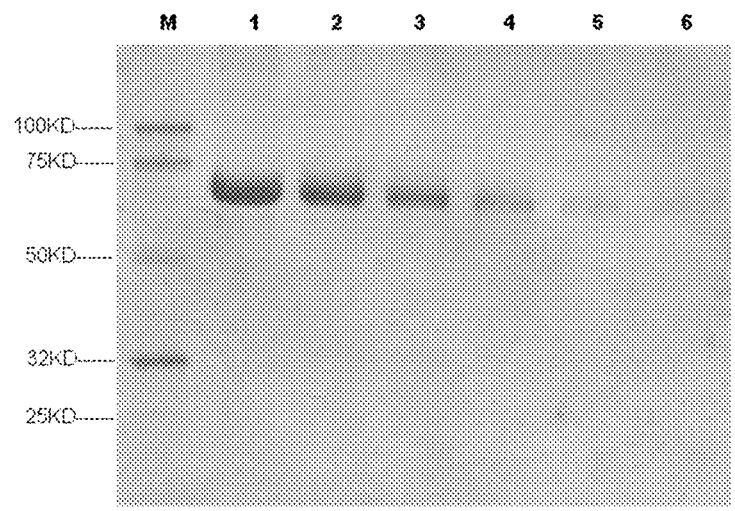
FIG. 3 is a picture of a SDS-PAGE gel after the quick Coomassie Blue staining procedure of FIG. 2; the gel is embedded with protein markers (GenScript MM0900; Lane M) and BSA protein at 1500 ng, 750 ng, 300 ng, 150 ng, 75 ng and 30 ng, in lanes 1 to 6, respectively.

A biopolymer can be embedded in a matrix by any method. In one embodiment of the present invention, the biopolymer is embedded in the matrix by electrophoresis, i.e., by applying an electrophoresis-electric force to the biopolymer to thus move it into the matrix, thereby embedding the biopolymer in the matrix. For example, as shown in FIGS. 2 and 3, a protein can be embedded in a polyacrylamide gel by loading a sample containing the protein into a loading well, applying an electric force to the protein to thus move the protein into the gel.

In embodiments according to FIGS. 5 and 6, the electric force used to embed the protein in the gel is transverse to the electric force used to move the staining reagent into the gel.

The invention also provides kits comprising one or more components useful for performing a staining or binding assays and instructions for using the components in carrying out a method of the invention. In one embodiment, the kit is compartmentalized to receive the one or more components. In yet another embodiment, the kit can comprise a device for performing quick protein staining assays.

In an embodiment of the present invention, the kit comprises staining solutions and optionally one or more other buffer solutions and instructions for using the solutions in a quick biopolymer staining assay according to an embodiment of the invention. The solutions can be provided in the kit in bottles or containers. The solutions can also be provided in the kit in solid porous materials, such as in pads, pre-absorbed with the solutions.

In other general aspects of the present invention, biopolymers other than peptides or proteins can also be stained using similar methods in view of the present disclosure. For example, an RNA, a DNA or a complex containing DNA or RNA, embedded in a matrix, such as an agarose gel or a polyacrylamide gel, can be stained by a staining reagent for nucleotides, such as an intercalating dye, preferably an intercalating fluorescent dye, using methods of the invention. Examples of the intercalating dyes include, but are not limited to, fluorescent dyes SYTO 61 (Invitrogen Corporation) and TOTO-3 (Invitrogen Corporation), ethidium bromide or propidium iodide.

In another embodiment of the present invention, an RNA, a DNA or a complex containing DNA or RNA, embedded in a matrix can be labeled by a labeling polynucleotide, e.g., a labeled polynucleotide probe, using a method according to the present invention. For example, an electric force can be applied to the labeled probe to move it into the matrix embedded with the DNA, the RNA, or the complex, to thereby hybridize with the DNA, the RNA or the complex in the matrix with reduced time.

It is readily appreciated by those skilled in the art that, similar methods can also be generally applied for interacting, reacting, binding or staining of a target molecule with a charged molecule. The target molecule is embedded in a matrix. An electric force moves the charged molecule into the matrix to thus interact, react, bind or stain the target molecule in the matrix.

Various embodiments of the invention have now been described. It is to be noted, however, that this description of these specific embodiments is merely illustrative of the principles underlying the inventive concept. It is therefore contemplated that various modifications of the disclosed embodiments will, without departing from the spirit and scope of the invention, be apparent to persons skilled in the art.

The following specific examples are further illustrative of the nature of the invention, it needs to be understood that the invention is not limited thereto.

EXAMPLE

Protein Staining

Protein markers (GenScript MM0900) and bovine serum albumin (BSA) at various amount, 1500 ng, 750 ng, 300 ng, 150 ng, 75 ng and 30 ng were loaded onto two mini SDS-PAGE gels in Lane M, Lane 1, Lane 2, Lane 3, Lane 4, Lane 5 and Lane 6, respectively. Electrophoresis was conducted to separate and embed the markers and BSA in the gels.

After the electrophoresis, one gel was stained using the quick staining procedure according to an embodiment of the present invention. The SDS-PAGE apparatus was disassembled. A quick staining system as shown in FIG. 5 was assembled. Buffer A contains, per liter of Buffer A, 200 grams acetic acid, 250 grams isopropanol, 10 grams EDTA, 6 grams Tris, and the pH is about 3.5. Buffer B contains 0.5% (wt/wt) of Coomassie blue R-250 in addition to the other ingredients of Buffer A. Buffer C contains, per liter of Buffer C, 20 grams sodium phosphate, monobasic, and 1 gram EDTA, and the pH is about 6.5. Electricity was applied to the quick staining system via the electrodes. The staining procedure was conducted at 20 volts for 6 minutes. FIG. 3 is a picture of the gel stained by Coomassie Blue using the quick staining procedure, which took only about 6 minutes.

Figure 4:
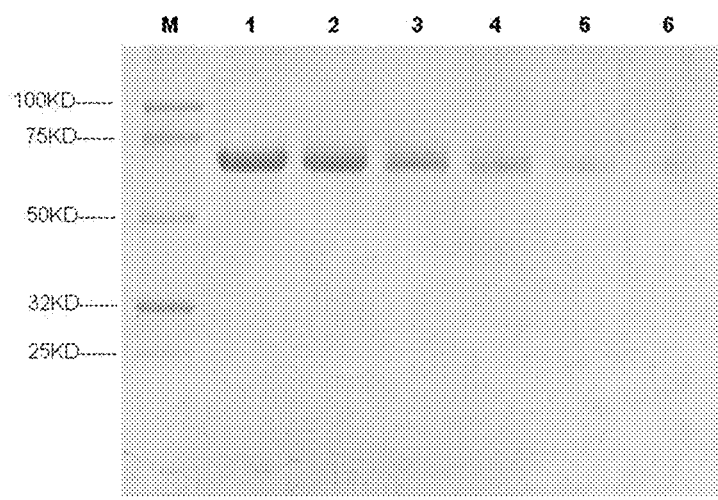
FIG. 4 is a picture of a SDS-PAGE gel after the conventional Coomassie Blue staining procedure of FIG. 1; the gel is embedded with protein markers (GenScript MM0900; Lane M) and BSA protein at 1500 ng, 750 ng, 300 ng, 150 ng, 75 ng and 30 ng, in lanes 1 to 6, respectively.

After the electrophoresis, another gel was stained using the conventional staining procedure. The SDS-PAGE apparatus was disassembled. The gel was fixed in a gel-fixing solution (100 ml of 10% acetic acid and 20% methanol in water) for 1 hr with gentle agitation. At the end of fixing, the gel-fixing solution was removed by aspiration. Staining solution (0.1% Coomassie blue R-250, 25% methanol and 10% acetic acid in water), 100 ml, was added to the gel. The gel was stained for 1 hr with gentle agitation. The staining solution was removed by aspiration. Destaining solution (25% methanol and 10% acetic acid in water), 100 ml, was added to the gel to destain the gel for 1 hr with gentle agitation. The destaining step was repeated 3 times until the protein bands were seen without background. FIG. 4 is a picture of the gel stained by Coomassie Blue using the conventional staining procedure, which took about 5 hours, 50 times of that used in the quick staining method.

FIGS. 3 and 4 show that the quick staining method according to an embodiment of the present invention achieved comparable result as that obtained by the conventional staining method, but in drastically reduced amount of time.

FIG. 6 illustrates an alternative quick staining system, which is similar to that illustrated in FIG. 5, except that the blotting paper presoaked in Buffer A is omitted.

All publications and patents referred to herein are incorporated by reference. Various modifications and variations of the described subject matter will be apparent to those skilled in the art without departing from the scope and spirit of the invention. Although the invention has been described in connection with specific embodiments, it should be understood that the invention as claimed should not be unduly limited to these embodiments. Indeed, various modifications for carrying out the invention are obvious to those skilled in the art and are intended to be within the scope of the following claims.

We claim:

1. An integrated method for staining a target molecule with a staining reagent, the method comprising: moving the target molecule into a matrix by applying a first electric force to the target molecule to obtain a matrix embedded with the target molecule; moving the staining reagent into the matrix embedded with the target molecule by applying a second electric force to the staining reagent, and moving excess free staining reagent out of the matrix by applying the second electric force to the excess free staining reagent, wherein the staining reagent stains the target molecule in the matrix, and the first electric force is transverse to the second electric force.

2. A method of staining a biopolymer, the method comprising: moving the biopolymer into a matrix by applying a first electric force to the biopolymer to obtain a matrix embedded with the biopolymer; moving a staining reagent into the matrix embedded with the biopolymer by applying a second electric force to the staining reagent, wherein the staining reagent stains the biopolymer in the matrix; and moving excess free staining reagent out of the matrix by applying the second electric force to the excess free staining reagent, thereby destaining the matrix, wherein the first electric force is transverse to the second electric force.

3. The method of claim 2, wherein the second electric force moves the staining reagent in a direction that the free excess staining reagent enters the matrix and travels the least distance in the matrix before leaving the matrix as compared to the other directions.

4. The method of claim 2, wherein the matrix is selected from the group consisting of an agarose gel, a polyacrylamide gel, and any porous material; the biopolymer is selected from the group consisting of a peptide, a protein, an RNA, a DNA, an oligosaccharide, and a complex thereof; and the staining reagent is a charged molecule selected from the group consisting of an organic or inorganic reagent, a dye or a dye-labeled reagent, a fluorescent molecule, a radioactive or radioactive-labeled reagent, an antibody or an antibody-based reagent, a labeled peptide or ligand, and a labeled polynucleotide.

5. The method of claim 2, further comprising moving a second staining reagent into the matrix embedded with the biopolymer by applying a the second electric force to the second staining reagent, wherein the biopolymer is stained with the second staining reagent in the matrix; and moving excess free second staining reagent out of the matrix by applying the second electric force to the excess free second staining reagent, thereby destaining the matrix.

6. The method of claim 2, wherein the staining reagent is dissolved or suspended in a solution or buffer or absorbed in a solid porous material prior to being moved into the matrix.

7. The method of claim 6, wherein the biopolymer is a protein or peptide; the matrix is a native or sodium dodecyl sulfate polyacrylamide gel; the staining reagent is selected from the group consisting of an organic dye, an inorganic dye, a fluorescent dye, a metal-complex dye, an antibody or an antibody-based reagent, and a labeled peptide or ligand; and the solid porous material is a blotting paper having a thickness of about 0.1 mm to about 20 mm.

8. A method of staining a biopolymer embedded in a matrix, the method comprising:
    assembling a staining system comprising:
        (i) a first solid porous material absorbed with a staining solution comprising a staining reagent;
        (ii) a matrix embedded with the biopolymer; and
        (iii) optionally one or more solid porous materials absorbed with one or more buffer solutions;
    interposing the staining system between a pair of electrodes; and
    moving the staining reagent into the matrix embedded with the biopolymer by applying an electric force to the staining reagent using the pair of electrodes, wherein the staining reagent stains the biopolymer in the matrix; and
    moving excess free staining reagent out of the matrix by applying the electric force to the excess free staining reagent, thereby destaining the matrix,
    wherein the first solid porous material, the matrix embedded with the biopolymer and the pair of electrodes are assembled such that the electric force moves the staining reagent in a direction that the excess free staining reagent enters the matrix and travels the least distance in the matrix before leaving the matrix as compared to the other directions.

9. The method of claim 8, wherein the matrix is selected from the group consisting of an agarose gel, a polyacrylamide gel, and any porous material; the biopolymer is selected from the group consisting of a peptide, a protein, an RNA, a DNA, an oligosaccharide, and a complex thereof; and the staining reagent is a charged molecule selected from the group consisting of an organic or inorganic reagent, a dye or a dye-labeled reagent, a fluorescent molecule, a radioactive or radioactive-labeled reagent, an antibody or an antibody-based reagent.

10. The method of claim 8, wherein the biopolymer is a protein or peptide; the matrix is a native or sodium dodecyl sulfate polyacrylamide gel; the staining reagent is selected from the group consisting of an organic dye, an inorganic dye, a fluorescent dye, a metal-complex dye, and an antibody or an antibody-based reagent; and the solid porous material is a blotting paper having a thickness of about 0.1 mm to about 20 mm.

11. The method of claim 10, wherein the staining reagent is an organic dye selected from the group consisting of Coomassie Blue, Amido black, Ponceaus S, Fast green FCF, zincon, Eriochrome black T, Colloidal Coomassie Blue, and derivatives thereof.

12. The method of claim 8, wherein the staining system comprises, in the following order:
    the first solid porous material absorbed with Solution B, which comprises, per liter of Solution B, about 10 grams to about 300 grams acetic acid, about 10 grams to about 500 grams isopropanol, about 0.1 gram to about 10 grams EDTA, about 0.1 gram to about 10 grams Tris, about 0.1 gram to 5 grams Coomassie Blue R-250 or Coomassie Blue G-250, about 0.1 gram to about 10 grams $Na_2HPO_4$, and about 0.1 gram to about 10 grams NaCl, and the pH being in the range of about 2.0- about 11.0;
    the polyacrylamide gel embedded with the protein or peptide; and a solid porous material absorbed with Solution C, which comprises, per liter of Solution C, about 1 gram to about 50 grams sodium phosphate, monobasic, and the pH being in the range of about 2.0- about 10.0;

wherein the pair of electrodes are connected to the first solid porous material and the solid porous material absorbed with Solution C, respectively.

13. The method of claim 12, wherein the staining system further comprises:

a solid porous material absorbed with a Solution A, which comprises, per liter of Solution A, about 10 grams to about 300 grams acetic acid, about 10 grams to 500 grains isopropanol, about 0.1 gram to about 10 grams EDTA, about 0.1 gram to about 10 grains per Tris, about 0.1 gram to about 10 grams $Na_2HPO_4$, and about 0.1 gram to about 10 grams NaCl, and the pH being the range of about 2.0-about 11.0, wherein the solid porous material absorbed with Solution A is placed adjacent to the first solid porous material, and the pair of electrodes are connected to the solid porous material absorbed with Solution A and the solid porous material absorbed with Solution C, respectively.

14. The method of claim 8, wherein the first solid porous material is further absorbed with a second staining solution comprising a second staining reagent, the staining reagent and the second staining reagent have the same charge type, and wherein the electric force is sufficient to move the first staining reagent and the second staining reagent into the matrix through the same surface of the matrix, thereby staining the biopolymer with both staining reagents in the matrix, and to move excess free staining reagents out of the matrix, thereby destaining the matrix.

15. The method of claim 8, wherein the staining system further comprises a second solid porous material absorbed with a second staining solution comprising a second staining reagent, the staining reagent and the second staining reagent have the same charge type, and the first and the second solid porous materials are placed to the same side of the matrix, and wherein the electric force is sufficient to move the staining reagent and second staining reagent into the matrix through the same surface of the matrix, thereby staining the biopolymer with both staining, reagents in the matrix, and to move excess free staining reagents out of the matrix, thereby destaining the matrix.

16. The method of claim 8, wherein the staining system further comprises a second solid porous material absorbed with a second staining solution comprising a second staining reagent, the first and the second staining reagents have opposite charge types, and the matrix is interposed between the first and the second solid porous materials, and wherein the electric force is sufficient to move the staining reagent and second staining reagent into the matrix through opposing surfaces of the matrix, thereby staining the biopolymer with both staining reagents in the matrix, and to move excess free staining reagents out of the matrix, thereby destaining the matrix.

17. The method of claim 8, wherein the biopolymer is embedded in the matrix by a method comprising applying an electrophoresis-electric force to move the biopolymer into the matrix, thereby embedding the biopolymer in the matrix, wherein the electrophoresis-electric force is applied to the matrix in a direct transverse to the direction of the electric force.

18. A method of staining a peptide or protein comprising:

moving a staining reagent into a matrix embedded with the peptide or protein by applying an electric force to the staining reagent, wherein the staining reagent stains the peptide or protein in the matrix; and moving excess free staining reagent out of the matrix by applying the electric force to the excess free staining reagent, thereby destaining the matrix, wherein the staining reagent is an organic dye selected from the group consisting of Coomassie Blue, Amido black, Ponceaus S, Fast green FCF, zincon, Eriochrome black T, Colloidal Coomassie Blue, and derivatives thereof, and the electric force moves the staining reagent in a direction such that the excess free staining reagent enters the matrix and travels the least distance in the matrix before leaving the matrix as compared to the other directions.

19. A method of staining a biopolymer, the method comprising:

moving a staining reagent into a matrix embedded with the biopolymer by applying an electric force to the staining reagent, wherein the staining reagent stains the biopolymer in the matrix; and moving excess free staining reagent out of the matrix by applying the electric force to the excess free staining reagent, thereby destaining the matrix, wherein the biopolymer is selected from the group consisting of an RNA, a DNA, an oligosaccharide and a complex thereof, and the electric force moves the staining reagent in a direction such that the excess free staining reagent enters the matrix and travels the least distance in the matrix before leaving the matrix as compared to the other directions.

* * * * *